US006546284B2

(12) United States Patent
Plummer

(10) Patent No.: US 6,546,284 B2
(45) Date of Patent: Apr. 8, 2003

(54) FLUID RETENTION ASSEMBLY FOR AN IONTOPHORETIC DELIVERY DEVICE AND ASSOCIATED METHOD FOR PREPARING THE SAME

(75) Inventor: Thomas L. Plummer, Salt Lake City, UT (US)

(73) Assignee: Iomed, Inc., Salt Lake City, UT (US)

( * ) Notice: Subject to any disclaimer, the term of this patent is extended or adjusted under 35 U.S.C. 154(b) by 0 days.

(21) Appl. No.: 09/769,657

(22) Filed: Jan. 25, 2001

(65) Prior Publication Data

US 2002/0099321 A1 Jul. 25, 2002

(51) Int. Cl.[7] .................................................. A16N 5/00
(52) U.S. Cl. ............................. 604/20; 128/770; 606/3; 606/9; 606/10; 606/17; 607/88
(58) Field of Search .................... 604/20, 21; 128/770; 606/2–17; 607/88–89

(56) References Cited

U.S. PATENT DOCUMENTS

| | | | |
|---|---|---|---|
| 4,553,966 A | | 11/1985 | Korteweg |
| 5,476,511 A | * | 12/1995 | Gwon et al. ................ 356/317 |
| 5,904,144 A | * | 5/1999 | Hammang et al. .......... 128/898 |
| 6,315,772 B1 | * | 11/2001 | Marchitto et al. ............ 604/21 |

OTHER PUBLICATIONS

IVALON Opthalmic Products promotional material (no date avail).
IVALON Product List promotional material (no date avail.).

* cited by examiner

Primary Examiner—Steven O. Douglas
(74) Attorney, Agent, or Firm—Factor & Partners

(57) ABSTRACT

A fluid retention assembly for use in association with an iontophoretic drug delivery device comprising: a matrix, wherein the matrix is fabricated from a hydroxylated polyvinyl acetal; a first excipient associated with the matrix, wherein the first excipient comprises a substantially non-ionic thickening agent; and a second excipient associated with the matrix, wherein the second excipient comprises a hydration enhancer.

A method for preparing a fluid retention assembly for use in association with an iontophoretic drug delivery device comprising the steps of: providing a first excipient, wherein the first excipient comprises a substantially non-ionic thickening agent; providing a second excipient, wherein the second excipient comprises a hydration enhancer; preparing a solution of the first and second excipients in a solvent; soaking a matrix fabricated from a hydroxylated polyvinyl acetal in the prepared solution; and drying the matrix.

31 Claims, 1 Drawing Sheet

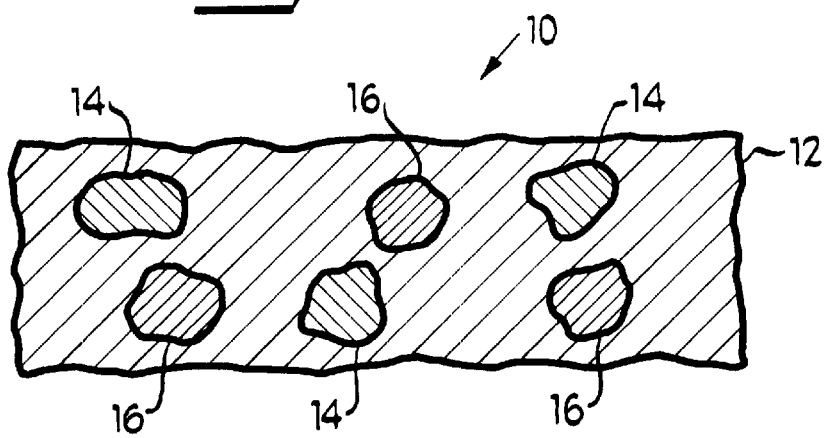
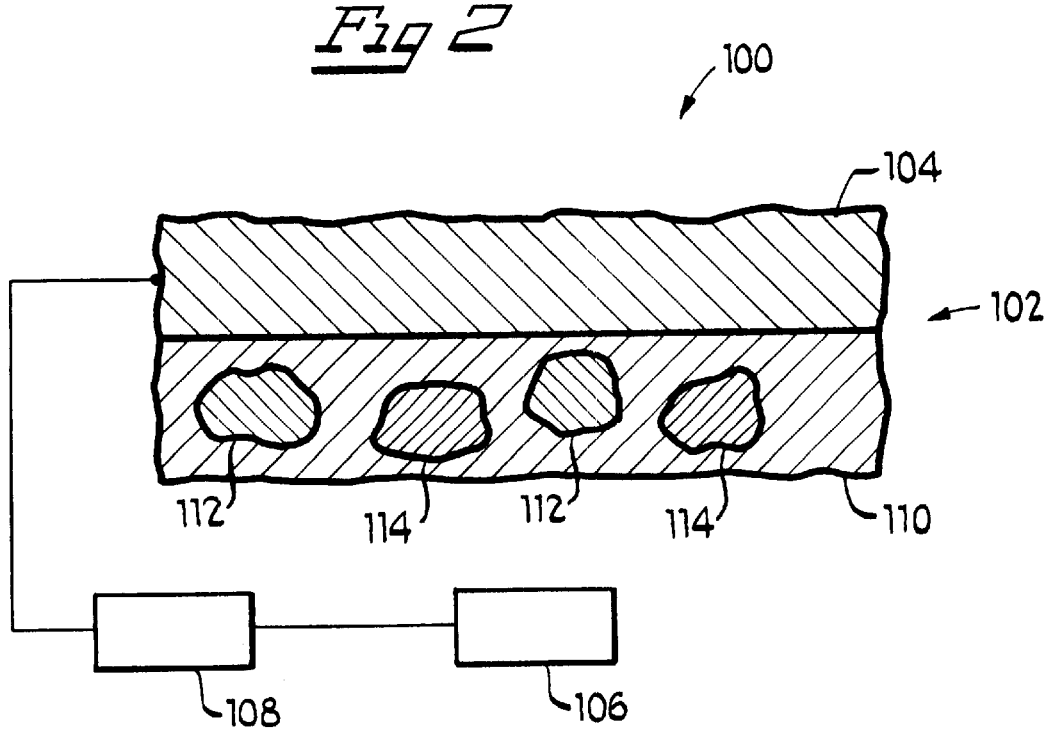

FLUID RETENTION ASSEMBLY FOR AN IONTOPHORETIC DELIVERY DEVICE AND ASSOCIATED METHOD FOR PREPARING THE SAME

BACKGROUND OF THE INVENTION

1. Field of the Invention

The present invention relates in general to a fluid retention assembly, and more particularly, to a fluid retention assembly having a matrix for use in association with an iontophoretic delivery device which, is configured for, among other things, ocular applications.

2. Background Art

Fluid retention assemblies having a matrix for use in association with iontophoretic delivery devices have been known in the art for several years. While conventional matrices of fluid retention assemblies have become commercially available, their use in especially sensitive applications, such as the ophthalmic administration of a medicament, or the administration a medicament to broken or otherwise damaged skin remains problematic. In particular, conventional matrices used in non-sensitive applications are fabricated from materials which can be too abrasive, contain too many particulates, and/or facilitate a undesirable degree of irritation for especially sensitive applications. For example, conventional matrices may scratch the surface of a patient's eye, or may further irritate a broken or damaged surface of a patient's body. Furthermore, conventional matrices may leave residual particulates and/or lint, which can be especially troublesome for ophthalmic applications. As such, there is a demand for a fluid retention assembly having a matrix, which is configured for sensitive iontophoretic applications, including ocular iontophoretic applications.

SUMMARY OF THE INVENTION

The present invention is directed to a fluid retention assembly for use in association with an iontophoretic drug delivery device comprising: (a) a matrix, wherein the matrix is fabricated from a hydroxylated polyvinyl acetal; (b) a first excipient associated with the matrix, wherein the first excipient comprises a substantially non-ionic thickening agent; and (c) a second excipient associated with the matrix, wherein the second excipient comprises a hydration enhancer.

In a preferred embodiment of the present invention, the first excipient comprises a cellulose ether, such as a hydroxypropylcellulose.

In another preferred embodiment of the present invention, the second excipient comprises an oxyalkylene polymer, such as a polyethylene glycol. Preferably, the polyethylene glycol has an average molecular weight ranging from approximately 1,000 to approximately 9,000.

In yet another preferred embodiment of the present invention, the matrix further comprises a therapeutic amount of a medicament, such as, but not limited to, a VEGF-inhibiting aptamer, an alpha-interferon, a beta-interferon, a gamma-interferon, dexamethasone sodium phosphate, lidocaine hydrochloride, amikacin, and/or gangcyclovir.

The present invention is also directed to an ocular iontophoretic drug delivery device comprising: (a) a fluid retention assembly comprising: (1) a matrix, wherein the matrix is fabricated from a hydroxylated polyvinyl acetal; (2) a first excipient associated with the matrix, wherein the first excipient comprises a substantially non-ionic thickening agent; and (3) a second excipient associated with the matrix, wherein the second excipient comprises a hydration enhancer; (b) an active electrode assembly associated with the fluid retention assembly; (c) a counter electrode assembly, wherein the counter electrode assembly is configured for completing an electrical circuit between the active electrode assembly and an energy source; and (d) an energy source for generating an electrical potential difference.

The present invention is further directed to a method for preparing a fluid retention assembly for use in association with an iontophoretic drug delivery device comprising the steps of: (a) providing a first excipient, wherein the first excipient comprises a substantially non-ionic thickening agent; (b) providing a second excipient, wherein the second excipient comprises a hydration enhancer; (c) preparing a solution of the first and second excipients in a solvent; (d) impregnating a matrix fabricated from a hydroxylated polyvinyl acetal with the prepared solution; and (e) drying the matrix.

In a preferred embodiment of the invention, the method further comprises the steps of associating a medicament with the matrix, such as a VEGF-inhibiting aptamer, an alpha-interferon, a beta-interferon, a gamma-interferon, dexamethasone sodium phosphate, lidocaine hydrochloride, amikacin, gangcyclovir, and/or mixtures thereof.

In another preferred embodiment of the present invention, the step of drying the matrix includes the steps of: (a) air drying the matrix at ambient temperature for approximately 15 hours; and (b) heating the matrix in an oven to approximately 50 degrees centigrade for approximately 2 hours after the step of air drying the same.

In yet another preferred embodiment of the present invention, the method further comprises the step of freezing the matrix after the step of drying the same.

BRIEF DESCRIPTION OF THE DRAWINGS

The invention will now be described with reference to the drawings wherein:

FIG. 1 of the drawings is a cross-sectional schematic representation of a first embodiment of a fluid retaining member fabricated in accordance with the present invention; and FIG. 2 of the drawings is a cross-sectional schematic representation of a first embodiment of an ocular iontophoretic device fabricated in accordance with the present invention.

DETAILED DESCRIPTION OF THE INVENTION

While this invention is susceptible of embodiment in many different forms, there is shown in the drawings and will herein be described in detail several specific embodiments with the understanding that the present disclosure is to be considered as an exemplification of the principles of the invention and is not intended to limit the invention to the embodiments illustrated.

Referring now to the drawings and to FIG. 1 in particular, a first embodiment of a fluid retention assembly 10 is shown, which generally comprises matrix 12, first excipient 14, and second excipient 16. It will be understood that FIG. 1 is merely a cross-sectional schematic representation of fluid retention assembly 10. As such, some of the components have been distorted from their actual scale for pictorial clarity. As will be discussed in greater detail below, fluid retention assembly 10 is configured for use in association an iontophoretic drug delivery device.

Matrix 12 is fabricated from a hydroxylated polyvinyl acetal, which is commercially available from, among other chemical vendors, M-Pact Worldwide, Inc., of Eudora, Kansas. Prior to association with the first and second excipients, matrix 12 is relatively non-malleable. However, after association with first and second excipients, matrix 12 is malleable, non-abrasive—even to highly sensitive areas, such as the surface of a patient's eye or a broken or otherwise damaged surface of a patient's body. Moreover, matrix 12 leaves little or no residual particulates or lint, facilitates little or no irritation to the administered area of the patient, and exhibits high hydration capacity—greater then approximately 7X w/w. Matrix 12 may be configured into any one of a number of geometric configurations depending upon the particular application.

For purposes of the present disclosure, first excipient 14 is associated with matrix 12 and comprises a substantially non-ionic thickening agent. In particular, first excipient 14 may comprise a cellulose ether, such as hydroxypropylcellulose, which is commercially available from Hercules, Inc., of Wilmington, Del. First excipient 14 primary serves to increase the viscosity of a medicament so that during administration of the medicament, weeping or dripping is minimized. First excipient 14 also serves to increase the lubricity of the matrix. While specific examples of first excipient 14 have been disclosed, for illustrative purposes only, it will be understood that other substantially non-ionic thickening agents that would be known to those having ordinary skill in the art having the present disclosure before them are likewise contemplated for use.

Second excipient 16 is also associated with matrix 12 and comprises a hydration enhancer. Preferred examples of hydration enhancers include oxyalkylene polymers, such as polyethylene glycol, which is commercially available from Union Carbide Corporation of Danbury, Conn. Although, polyethylene glycol having various average molecular weights are operable in accordance with the present invention, polyethylene glycols having an average molecular weight ranging from approximately 1,000 to approximately 9,000 are preferred. Second excipient 16 primary serves to increase the lubricity of the matrix so that during administration of the medicament, irritation and/or dryness is minimized. While specific examples of second excipient 16 have been disclosed, for illustrative purposes only, it will be understood that other hydration enhancers that would be known to those having ordinary skill in the art having the present disclosure before them are likewise contemplated for use.

Although not shown, matrix 12 may also include a medicament to treat an affected area of a living being's body, such as an eye. Examples of medicaments include a VEGF-inhibiting aptamer, an alpha-interferon, a beta-interferon, a gamma-interferon, dexamethasone sodium phosphate, lidocaine hydrochloride, amikacin, gangcyclovir, and/or mixtures thereof.

Matrix 12 may also contain supplemental agents, such as electrolytes, stability additives, medicament preserving additives, pH regulating buffers—just to name a few.

Referring now to FIG. 2, ocular iontophoretic drug delivery device 100 is shown which generally comprises fluid retention assembly 102, active electrode assembly 104, counter electrode assembly 106, and energy source 108.

Fluid retention assembly 102 is configured in an analogous manner to fluid retention assembly 12 and includes matrix 110, first excipient 112, and second excipient 114.

Active electrode assembly 104 generally comprises a conductive material, it which upon application of an electrical potential difference thereto, drives an ionic medicament, within matrix 110 and delivers the medicament into predetermined tissues and surrounding structures of a living being. It will be understood that active electrode assembly 104 may comprise an anode or a cathode depending upon whether the medicament is cationic or anionic in form. It will be further understood that active electrode assembly may include an open-faced or high current density electrode. As would be readily understood to those having ordinary skill in the art, any one of a number of conventional active electrode assemblies are contemplated for use in accordance with the present invention. The only contemplated limitation relative to active electrode assembly 104 is that it must be geometrically and compositionally compatible for ocular and/or non-ocular applications of living beings, most relevantly, humans.

Counter electrode assembly 106 may be housed within ocular iontophoretic device 100, or alternatively, may be remotely associated with ocular iontophoretic device 100 via conventional electrical conduit. Counter electrode assembly 106 is configured for completing an electrical circuit between active electrode assembly 104 and energy source 108. As with active electrode assembly 104, counter electrode assembly 106 may comprise an anode or a cathode depending upon whether the medicament is cationic or anionic in form. As would be readily understood to those having ordinary skill in the art, any one of a number of counter electrodes are contemplated for use in accordance with the present invention.

Similarly to counter electrode assembly 106, energy source 108 may be housed within ocular iontophoretic device 100, or alternatively, may be remotely associated with ocular iontophoretic device 100 via conventional electrical conduit. Energy source 108 preferably supplies low voltage direct current between approximately 0.1 milliamps (mA) and approximately 10 mA for generating an electrical potential difference. The energy source may also provide for an initial higher voltage during current ramp-up to break down higher initial tissue resistance as in commercial power supply units used for transdermal iontophoresis. For purposes of the present disclosure, energy source 108 may include one or more primary or secondary electrochemical cells. While specific examples of energy source 108 have been disclosed, for illustrative purposes only, it will be understood that other energy sources known to those having ordinary skill in the art having the present disclosure before them are likewise contemplated for use.

The present invention is also directed to a method for preparing a fluid retention assembly for use in association with an iontophoretic drug delivery device comprising the following steps. At the outset, a first excipient is provided which comprises a substantially non-ionic thickening agent, including cellulose ethers, such as hydroxypropylcellulose. Next, a second excipient is provided which comprises a hydration enhancer, including oxyalkylene polymers, such as polyethylene glycol having an average molecular weight ranging from approximately 1,000 to approximately 9,000. Third, a solution is prepared by dissolving the second and first excipients in a solvent, such as purified water or other polar solvents. Preferably the concentration of the excipients ranges from approximately 0.5% to approximately 2% by weight. More preferably the concentration of the first excipient is approximately 1.75% by weight and the concentration of the second excipient is approximately 1.25% by weight.

After the above-identified solution has been prepared, a matrix fabricated from a hydroxylated polyvinyl acetal is impregnated with the solution. Once the matrix has been impregnated, it is dried.

Although drying the matrix may be carried using numerous methods, it has been found that freeze drying or air drying the matrix at ambient temperature for approximately 15 hours, followed by heating the matrix in an oven to approximately 50 degrees centigrade for approximately 2 hours substantially prevents any warping that may otherwise occur if the matrix is dried at elevated temperatures without first air-drying at ambient temperatures.

After the matrix has been dried, it may be placed in a freezer for storage until used at a later time.

At a time prior to use of the matrix, a medicament may be associated thereto using conventional techniques. Examples of some medicaments include a VEGF-inhibiting aptamer, an alpha-interferon, a beta-interferon, a gamma-interferon, dexamethasone sodium phosphate, lidocaine hydrochloride, amikacin, gangcyclovir, and/or mixtures thereof.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A fluid retention assembly for use in association with an iontophoretic drug delivery device, comprising:
   a matrix, wherein the matrix is fabricated from a hydroxylated polyvinyl acetal;
   a first excipient associated with the matrix, wherein the first excipient comprises a substantially non-ionic thickening agent; and
   a second excipient associated with the matrix, wherein the second excipient comprises a hydration enhancer.

2. The fluid retention assembly according to claim 1, wherein the first excipient comprises a cellulose ether.

3. The fluid retention assembly according to claim 1, wherein the first excipient comprises a hydroxypropylcellulose.

4. The fluid retention assembly according to claim 1, wherein the second excipient comprises an oxyalkylene polymer.

5. The fluid retention assembly according to claim 1, wherein the second excipient comprises a polyethylene glycol.

6. The fluid retention assembly according to claim 5, wherein the second excipient comprises a polyethylene glycol having an average molecular weight ranging from approximately 1,000 to approximately 9,000.

7. The fluid retention assembly according to claim 1, wherein the first excipient comprises a hydroxypropylcellulose, and the second excipient comprises a polyethylene glycol.

8. The fluid retention assembly according to claim 1, further comprising a medicament.

9. The fluid retention assembly according to claim 8, wherein the medicament is selected from at least one of the group consisting of a VEGF-inhibiting aptamer, an alpha-interferon, a beta-interferon, a gamma-interferon, dexamethasone sodium phosphate, lidocaine hydrochloride, amikacin, gangcyclovir, and/or mixtures thereof.

10. An ocular iontophoretic drug delivery device, comprising:
    a fluid retention assembly comprising:
       a matrix, wherein the matrix is fabricated from a hydroxylated polyvinyl acetal;
       a first excipient associated with the matrix, wherein the first excipient comprises a substantially non-ionic thickening agent; and
       a second excipient associated with the matrix, wherein the second excipient comprises a hydration enhancer;
    an active electrode assembly associated with the fluid retention assembly;
    a counter electrode assembly, wherein the counter electrode assembly is configured for completing an electrical circuit between the active electrode assembly and an energy source; and
    an energy source for generating an electrical potential difference.

11. The fluid retention assembly according to claim 10, wherein the first excipient comprises a cellulose ether.

12. The fluid retention assembly according to claim 10, wherein the first excipient comprises a hydroxypropylcellulose.

13. The fluid retention assembly according to claim 10, wherein the second excipient comprises an oxyalkylene polymer.

14. The fluid retention assembly according to claim 10, wherein the second excipient comprises a polyethylene glycol.

15. The fluid retention assembly according to claim 14, wherein the second excipient comprises a polyethylene glycol having an average molecular weight ranging from approximately 1,000 to approximately 9,000.

16. The fluid retention assembly according to claim 10, wherein the first excipient comprises a hydroxypropylcellulose, and the second excipient comprises a polyethylene glycol.

17. The fluid retention assembly according to claim 10, further comprising a medicament.

18. The fluid retention assembly according to claim 17, wherein the medicament is selected from at least one of the group consisting of a VEGF-inhibiting aptamer, an alpha-interferon, a beta-interferon, a gamma-interferon, dexamethasone sodium phosphate, lidocaine hydrochloride, amikacin, gangcyclovir, and/or mixtures thereof.

19. A method for preparing a fluid retention assembly for use in association with an iontophoretic drug delivery device, comprising the steps of:
    providing a first excipient, wherein the first excipient comprises a substantially non-ionic thickening agent;
    providing a second excipient, wherein the second excipient comprises a hydration enhancer;
    preparing a solution of the first and second excipients in a solvent;
    impregnating a matrix fabricated from a hydroxylated polyvinyl acetal with the prepared solution; and
    drying the matrix.

20. The method according to claim 19, wherein the step of providing a first excipient includes the step of providing a cellulose ether.

21. The method according to claim 19, wherein the step of providing a first excipient includes the step of providing a hydroxypropylcellulose.

22. The method according to claim 19, wherein the step of providing a second excipient includes the step of providing an oxyalkylene polymer.

23. The method according to claim 19, wherein the step of providing a second excipient includes the step of providing a polyethylene glycol.

24. The fluid retention assembly according to claim 19, wherein the second excipient comprises a polyethylene glycol having an average molecular weight ranging from approximately 1,000 to approximately 9,000.

25. The method according to claim 19, wherein the step of providing a first excipient includes the step of providing a hydroxypropylcellulose and the step of providing a second excipient includes the step of providing a polyethylene glycol having an average molecular weight ranging from approximately 1,000 to approximately 9,000.

26. The method according to claim 19, further comprising the step of associating a medicament with the matrix.

27. The method according to claim 19, further comprising the step of a associating a VEGF-inhibiting aptamer, an alpha-interferon, a beta-interferon, a gamma-interferon, dexamethasone sodium phosphate, lidocaine hydrochloride, amikacin, gangcyclovir, and/or mixtures thereof.

28. The method according to claim 19, wherein the step of drying the matrix includes the steps of:
    air drying the matrix at ambient temperature for approximately 15 hours; and
    heating the matrix in an oven to approximately 50 degrees centigrade for approximately 2 hours after the step of air drying the same.

29. The method according to claim 19, further comprising the step of freezing the matrix after the step of drying the same.

30. The method according to claim 19, wherein the step of drying the matrix includes the step of freeze drying the matrix.

31. A method for preparing a fluid retention assembly for use in association with an iontophoretic drug delivery device, comprising the steps of:
    providing a first excipient, wherein the first excipient comprises a substantially non-ionic thickening agent;
    providing a second excipient, wherein the second excipient comprises a hydration enhancer;
    preparing a solution of the first and second excipients in a solvent;
    impregnating a matrix fabricated from a hydroxylated polyvinyl acetal with the prepared solution; and
    substantially removing the solvent from the matrix.

* * * * *